United States Patent
Vilsmeier

(10) Patent No.: US 7,050,845 B2
(45) Date of Patent: May 23, 2006

(54) PROJECTING PATIENT IMAGE DATA FROM RADIOSCOPIC IMAGING METHODS AND/OR TOMOGRAPHIC IMAGING METHODS ONTO VIDEO IMAGES

(75) Inventor: Stefan Vilsmeier, Kufstein (AT)

(73) Assignee: BrainLAB AG, Kirchheim/Heimstetten (DE)

(*) Notice: Subject to any disclaimer, the term of this patent is extended or adjusted under 35 U.S.C. 154(b) by 422 days.

(21) Appl. No.: 10/134,977

(22) Filed: Apr. 29, 2002

(65) Prior Publication Data

US 2003/0114741 A1    Jun. 19, 2003

(30) Foreign Application Priority Data

Dec. 18, 2001  (EP)  .................... 01129381

(51) Int. Cl.
*A61B 5/05*  (2006.01)

(52) U.S. Cl. ...................... 600/427; 600/407

(58) Field of Classification Search ........... 600/427, 600/428, 429, 417, 407, 431, 432, 433, 434, 600/435; 666/130
See application file for complete search history.

(56) References Cited

U.S. PATENT DOCUMENTS

| | | |
|---|---|---|
| 5,526,812 A | 6/1996 | Dumoulin et al. |
| 5,694,142 A | 12/1997 | Dumoulin et al. |
| 5,715,836 A | 2/1998 | Kliegis et al. |
| 5,765,561 A | 6/1998 | Chen et al. |
| 5,961,456 A | 10/1999 | Gildenberg |
| 6,038,467 A | 3/2000 | De Bliek et al. |
| 6,477,400 B1 * | 11/2002 | Barrick ........................ 600/426 |
| 6,490,467 B1 * | 12/2002 | Bucholz et al. ............. 600/407 |
| 6,640,128 B1 * | 10/2003 | Vilsmeier et al. ........... 600/427 |
| 2001/0035871 A1 | 11/2001 | Bieger et al. |
| 2002/0082498 A1 | 6/2002 | Wendt et al. |
| 2002/0140694 A1 | 10/2002 | Sauer et al. |
| 2002/0163499 A1 | 11/2002 | Sauer |

FOREIGN PATENT DOCUMENTS

| | | |
|---|---|---|
| EP | 0 672 389 A2 | 9/1995 |
| EP | 0 672 389 | 8/1998 |
| WO | 96/20421 | 7/1996 |
| WO | 96/20421 A | 7/1996 |

OTHER PUBLICATIONS

Sauer, Frank et al. "Augmented Reality Visualization in iMRI Operating Room: System Description and Pre-clinical Testing." *Proceedings of SPIE, Medical Imaging*. Jan. 23-26, 2002.

* cited by examiner

*Primary Examiner*—Daniel Robinson
(74) *Attorney, Agent, or Firm*—Renner, Otto, Boisselle & Sklar, LLP

(57) ABSTRACT

The invention relates to a device for projecting patient image data from radioscopic imaging methods and/or tomographic imaging methods onto video images, comprising an image display device (10), at least one video camera (14) and a computer-assisted navigation system which can detect the spatial positions of the image display device (10) and/or the video camera (14) and the spatial positions of a part of a patient's body (1) via tracking means (12, 3) attached to it, wherein the image display device (10) and the video camera (14) are assigned to each other and are realized as a portable unit.

14 Claims, 2 Drawing Sheets

PROJECTING PATIENT IMAGE DATA FROM RADIOSCOPIC IMAGING METHODS AND/OR TOMOGRAPHIC IMAGING METHODS ONTO VIDEO IMAGES

The present invention relates to a device for projecting patient image data from radioscopic imaging methods and/or tomographic imaging methods onto video images. The device comprises an image display device, at least one video camera and a computer-assisted navigation system which can detect the spatial position of the image display device and/or the video camera and the spatial positions of a part of a patient's body via tracking means attached to it.

Such devices serve to visually assist a physician during diagnosis or while treating a patient. The option should be provided of combining images from the patient's interior with conventional video images, in order to facilitate treatment and diagnosis.

BACKGROUND OF THE INVENTION

A video-based surgical target system is known from U.S. Pat. No. 5,765,561, for which among other things the use of a tracked video camera is proposed, whose images are superimposed onto assigned images from radioscopic imaging methods and/or tomographic imaging methods on the statically arranged screen of a navigation system. A particular disadvantage of such an embodiment is that the physician wishing to view the images always has to look away from the patient, to the screen of the navigation system. He can then no longer pay exact attention to the position in which the camera is, i.e. the exterior position from which he is obtaining the superimposed images. The system is therefore somewhat awkward and does not enable direct inspection within the part of the patient's body.

SUMMARY OF THE INVENTION

The present invention provides a device for projecting patient image data from radioscopic imaging methods and/or tomographic imaging methods onto video images, which overcomes the disadvantages of the prior art cited above. In particular, it should be made possible for the treatment staff to obtain the desired image data directly and in direct view of the patient.

In accordance with the invention, an image display device and the video camera are assigned to each other and realized as a portable unit. Using this embodiment in accordance with the invention, the physician carrying out the treatment then has the option of holding the image display device, even with the assigned camera, in front of the part of the patient's body, and therefore of reading the desired anatomical information while looking directly at the patient. It is possible in this respect to adjust the video image or the image from the radioscopic imaging method and/or tomographic imaging method to be more or less transparent, as desired, in the image shown on the image display device, in order to highlight specifically the desired information most clearly within the display as a whole. Using the device in accordance with the invention, another step is taken towards creating a "glass patient", simply by holding the image display device in front of the relevant part of the patient's body. Since the camera assignment to the image display device is tracked via the tracking means, the position of these two elements is always known, and the navigation system has information on how and from which direction the part of the patient's body is being viewed. In particular when performing minimally invasive surgery in which the area of surgery is not exposed, the device in accordance with the invention thus offers the physician carrying out the treatment the option of again informing himself of the exact position of the parts of the patient's anatomy during the operation. In this way, tracked or navigated instruments can of course also been shown on the image display device. The physician no longer has to look away from the patient in order to look into the interior of the patient's body.

In accordance with a preferred embodiment of the invention, the video camera is arranged on the rear side of the image display device. This results in a compact apparatus; the camera can be completely removed from the operator's field of view. It should be noted in principle that the camera can be attached at any point on the rear side of the image display device, or can be integrated into it, for example even in the area of the edge of the image display device.

The video camera is preferably spatially assigned to the image display device in a way which is predetermined and/or known to the system, and the tracking means is arranged on the image display device. Spatially assigning the video camera and the image display device in a way which is predetermined and/or known to the system opens up the option of tracking just one of these two apparatus by means of the tracking means, since it is also known exactly where the other apparatus is situated. The designer is then also at liberty to arrange the tracking means either on the image display device itself or on the video camera, according to how said tracking means can best be detected by the navigation system. In optically based navigation systems, the tracking means can also be an arrangement of reflecting or actively emitting markers, although it is of course also possible within the context of the present invention to perform navigation via a magnetic tracking system in which coils are tracked in a generated magnetic field.

In order to design the image display device to be easy to handle, it can be designed as a portable LCD flat screen.

Data transmission between the individual apparatus of the device in accordance with the invention is realized in different ways. On the one hand, it is possible to communicate the image data from the radioscopic imaging method and/or tomographic imaging method to be projected onto the video images to the image display device via radio interfaces of the navigation system, while on the other hand communicating the data via data cables is also conceivable. One embodiment ought to prove particularly advantageous within the context of handling the device in accordance with the invention, in which the image display device is provided with its own energy supply (battery or power pack) and transmission is by radio, since this achieves the most extensive freedom of handling.

In accordance with a preferred embodiment, the video camera should exhibit a small aperture and a low depth of field, so that only a small area of the detected image is in the focal plane. Using such a camera, it is possible to determine the distance between the image and the focal plane. If the spatial position of the camera is known from the navigation system, and the distance from the image plane is also known, then the computer system connected to the navigation system can calculate the spatial position of the video image in real time. This enables the video image and the image data from a radioscopic imaging method and/or tomographic imaging method carried out beforehand to be optimally assigned.

In accordance with another advantageous embodiment of the device in accordance with the invention, a data transmission means is arranged on the video camera or on the image display device, wherein information on the image shown on the image display device is transmitted to the navigation system by means of said data transmission means. The image data to be projected, communicated from the navigation system to the image display device, are then adapted in size and position on the image display device such that they are in registration with the video images, i.e. a 1:1 representation of the two images in overlap is created. To this end, a contour-matching unit can be provided in the navigation system, said contour-matching unit superimposing the video images and the projected images, in particular via outer contour matching of the part of the patient's body.

It should also be noted here that it may be conceivable and advantageous within the context of the invention to attach to the portable unit many and various control apparatus and command input apparatus for altering the combined image shown. For example, the focal plane both of the radioscopic imaging method or tomographic imaging method employed and of the video image shown can be altered using such control elements. As already mentioned above, it is also possible to provide control elements which alter the respective degree of transparency of one of the images with respect to the other.

An illuminating device for the part of the patient's body is advantageously provided on the camera or in its vicinity on the image display device, especially for example as a ring light (LEDs, lamps, fluorescent tubes).

BRIEF DESCRIPTION OF THE DRAWINGS

The invention will now be described in more detail, by way of an embodiment. In the drawings provided for this purpose, there is shown.

DETAILED DESCRIPTION

Figure 1:
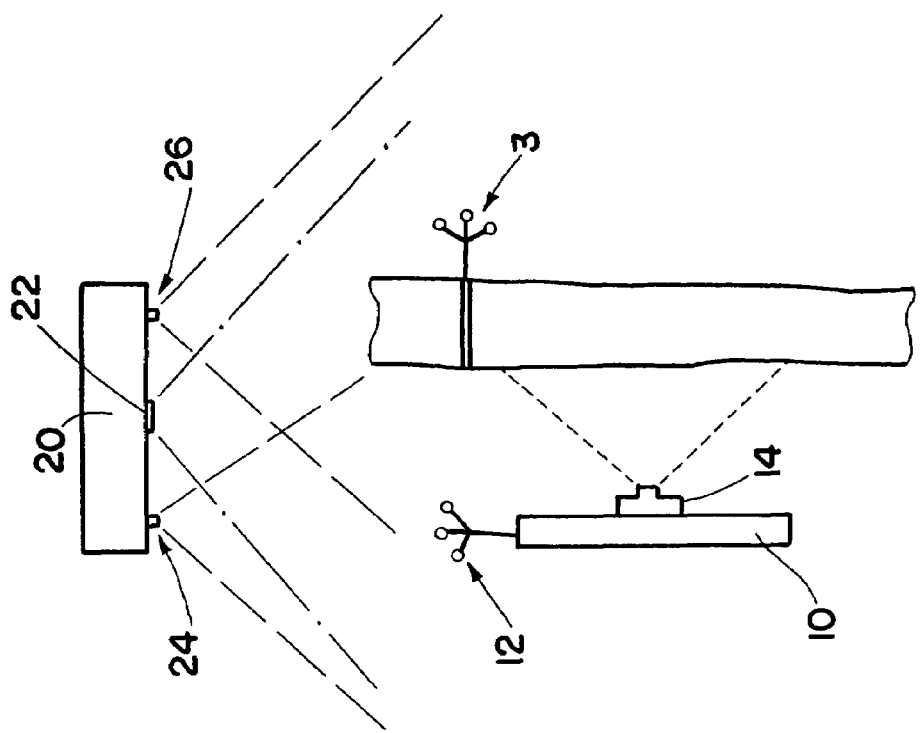
FIG. 1 a schematic representation of the use of a device in accordance with the invention for viewing the knee joint of a patient, in aspect.

FIG. 1 schematically shows a device in accordance with the invention, using which the interior of a patient's joint may for example be inspected. The leg 1 of the patient is to be examined at the joint 5. To this end, the flat screen 10 designed in accordance with the invention is held directly in front of the joint, and an image then appears on the screen 10 containing both image information from the video camera image of the camera 14 (FIG. 2) as well as image information on the interior anatomical structure, said information being communicated for example by a navigation apparatus, by radio. To this end, a tomographic image (MR or CT image) is produced beforehand of the patient or of the patient's leg 1.

Figure 2:
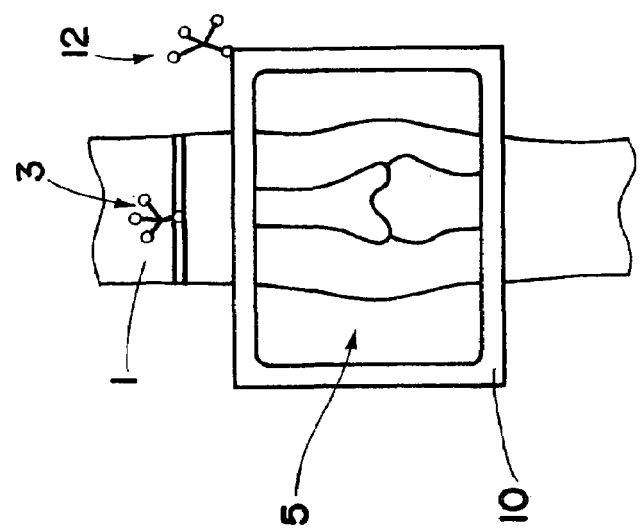
FIG. 2 a lateral view of the device according to FIG. 1, together with a schematically represented navigation system.

As is indicated more clearly in FIG. 2, the camera 14 is situated, firmly attached, on the rear side of the screen 10.

This type of image representation is made possible by the spatial position of the camera 14 or of the image screen 10 being tracked around the leg 1 of the patient by means of a tracking means. In the present case, this tracking means is an optical tracking means, namely an arrangement 12 of markers whose position is detected by means of the schematically represented navigation system 20. To this end, the navigation system 20 includes for example two spaced-out infrared cameras 24, 26 and an infrared light emitter 22. The three-dimensional spatial position of the arrangement 12 of markers, and therefore also of the screen 10 and the firmly installed camera 14, can be determined from the two images from the infrared cameras 24, 26. Furthermore, it is possible to determine the spatial position of the leg 1 using a corresponding arrangement 3 of markers.

If the position of the screen 10 and the camera 14 is then known, the position of the current image plane can be detected as follows. The camera 14 has, namely, a small aperture and a low depth of field, such that the image only appears in focus in a particular focal plane. This allows the position of said image plane to be determined and an image from the CT or MR imaging method to be transmitted on the screen 10, which is also exactly in said image plane. The important thing here is that the image ratio of the video image is shown at a scale of 1:1 with respect to the tomographic image. If the joint of a patient is then viewed using the device in accordance with the invention, one sees for example the contours of the patient's leg at the upper and lower edge of the screen. Using this information, the image from the tomographic imaging method can then be adapted such that it lies exactly over the video image, to ensure a realistic impression. The person viewing the screen 10 can then view on the screen both the video image, i.e. a real image, and the "interior" image from the tomographic imaging method, and in any desired depth and with any adjusted transparency of the two images. These adjustments can be made via control devices (not shown), for example flip switches on the front side of the screen.

For the first time, therefore, the device in accordance with the invention gives the observer the option of looking into the interior treatment area in real time while looking at the patient, and of planning or adapting the treatment accordingly. He no longer has to look away from the patient to a firmly installed navigation screen, which is particularly advantageous when the patient's responses to particular medical measures are to be tested. Since the "interior" images from the radioscopic imaging method and/or tomographic imaging method are formed such that they represent virtual 3-D views of the interior parts of the body, the image as a whole can be made very vivid.

Although a radioscopic and/or tomographic image is therefore not taken in situ, a virtual "glass patient" is thus created.

Figure 3:
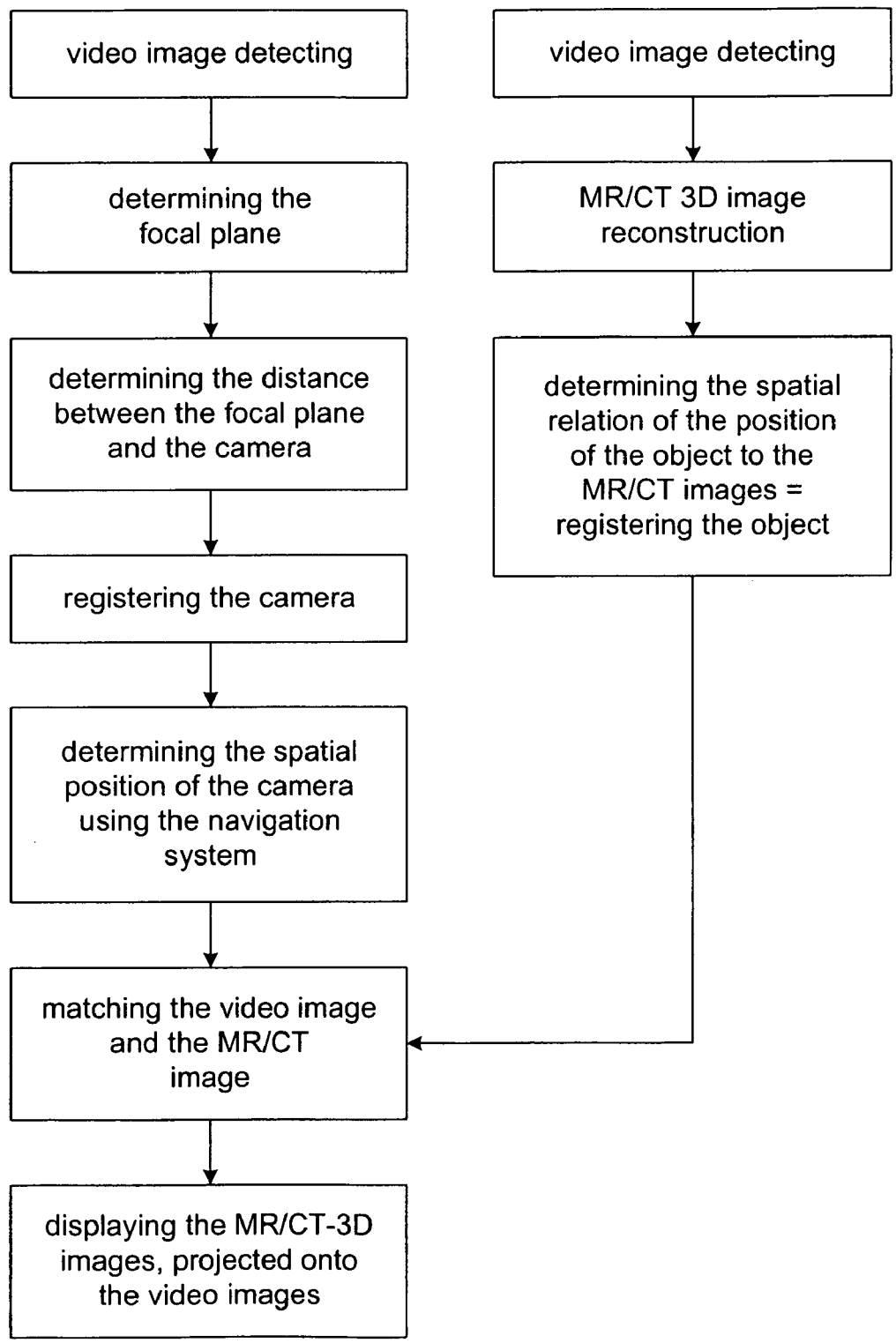
FIG. 3 a flow diagram of operating the device in accordance with the invention.

FIG. 3 shows the sequence of a method such as is performed using the device in accordance with the invention; the activity carried out by the computer of the navigation system is illuminated here in particular. The upper left side of the flow diagram relates to the processes in video image detection, while on the right-hand side image detection for the interior of the body is explained, using the example of MR/CT image detection. In video image detection, the focal plane is firstly determined, as has already been explained above. Then the distance from the focal plane to the camera is determined, whereupon the camera is registered by means of its tracking means in the navigation system. The determined spatial position of the camera with respect to the navigation system is then known.

With respect to MR/CT image detection, an MR/CT image is firstly detected beforehand, whereupon a three-dimensional image is reconstructed from the data obtained. Then, the object—for example, a part of the patient's body—is spatially registered, i.e. the spatial relation of the position of the object to the MR/CT images is determined. This can only be realized by spatially detecting an arrangement of markings situated on the object.

When the video image detection and MR/CT image processing steps cited above have been performed, then video/MR/CT-image matching is performed, i.e. the two images are harmonized under computer guidance, with respect to image position and image size. Then, the MR/CT/3-D images, projected onto the video images, can be superimposed on the image display device, and can assist the physician performing the treatment in diagnose and treatment.

What is claimed is:

1. A device for projecting patient image data from radioscopic imaging methods and/or tomographic imaging methods onto video images, comprising an image display device, at least one video camera, and a computer-assisted navigation system which can detect the spatial positions of said image display device and/or said video camera and the spatial positions of a part of a patient's body via tracking means attached to it, wherein said image display device and said video camera are assigned to each other and are realized as a portable unit.

2. The device as set forth in claim 1, wherein said video camera is arranged on the rear side of said image display device.

3. The device as set forth in claim 1, wherein said video camera is spatially assigned to said image display device in a way which is predetermined and/or known to the system.

4. The device as set forth in claim 1, wherein said video camera is spatially assigned to said image display device in a way which is predetermined and/or known to the system.

5. The device as set forth in claim 1, wherein said image display device is a portable LCD flat screen.

6. The device as set forth in claim 1, wherein the image data from said radioscopic imaging method and/or tomographic imaging method to be projected onto said video images are communicated to said image display device via radio interfaces of said navigation system.

7. The device as set forth in claim 1, wherein the image data from said radioscopic imaging method and/or tomographic imaging method to be projected onto said video images are communicated to said image display device via a data cable of said navigation system.

8. The device as set forth in claim 1, wherein said video camera exhibits a small aperture and a low depth of field.

9. The device as set forth in claim 1, wherein a data transmission means is arranged on said video camera or on said image display device, by means of which information on the image shown on said image display device is transmitted to said navigation system, wherein the image data to be projected, from said radioscopic imaging methods and/or tomographic imaging methods, communicated from said navigation system to said image display device, are adapted in size and position on said image display device such that they are in registration with said video images.

10. The device as set forth in claim 9, wherein said navigation system comprises a contour-matching unit which superimposes said video images and said projected images, in particular via outer contour matching of said part of the patient's body.

11. The device as set forth in claim 1, wherein an illuminating device for said part of the patient's body is provided on said camera or in its vicinity on said image display device.

12. The device as set forth in claim 1, wherein control apparatus and command input apparatus for altering the combined image shown are attached to the portable unit.

13. The device as set forth in claim 12, wherein the control apparatus and command input apparatus alter the focal plane both of the radioscopic or tomographic image data employed and of the video image shown.

14. The device as set forth in claim 12, wherein the control apparatus and command input apparatus alter the respective degree of transparency of one of the images with respect to the other.

* * * * *